United States Patent
Doody et al.

(10) Patent No.: US 7,991,260 B2
(45) Date of Patent: Aug. 2, 2011

(54) LIGHT-DIFFUSING SAFETY CAP

(75) Inventors: Michael C. Doody, Knoxville, TN (US); William T. Milam, Maryville, TN (US)

(73) Assignee: SensorMed, Inc., Knoxville, TN (US)

(*) Notice: Subject to any disclaimer, the term of this patent is extended or adjusted under 35 U.S.C. 154(b) by 0 days.

(21) Appl. No.: 12/906,468

(22) Filed: Oct. 18, 2010

(65) Prior Publication Data

US 2011/0034774 A1  Feb. 10, 2011

Related U.S. Application Data

(63) Continuation-in-part of application No. 12/435,479, filed on May 5, 2009.

(51) Int. Cl.
*G02B 6/00* (2006.01)
*G02B 6/42* (2006.01)
*G02B 6/32* (2006.01)
*G02B 6/36* (2006.01)
*G02B 6/06* (2006.01)

(52) U.S. Cl. .............. 385/139; 385/31; 385/32; 385/33; 385/34; 385/92; 385/93; 385/94; 385/116; 385/117; 385/119; 385/134; 385/140; 385/147

(58) Field of Classification Search .............. 385/31–34, 385/92–94, 116, 117, 119, 134, 139, 147, 385/901, 140, 14; 362/26, 551, 556, 558, 362/572, 574, 615, 610; 359/599; 606/15–17, 606/46; 600/101, 108, 119, 171, 175, 180

See application file for complete search history.

(56) References Cited

U.S. PATENT DOCUMENTS

| | | | |
|---|---|---|---|
| 3,675,984 A | 7/1972 | Vulmiere et al. | |
| 5,303,324 A | 4/1994 | Lundahl | |
| 5,329,938 A | 7/1994 | Lonky | |
| 6,332,092 B1 | 12/2001 | Deckert et al. | |
| 6,387,044 B1* | 5/2002 | Tachibana et al. | 600/114 |
| 6,398,778 B1 | 6/2002 | Gu et al. | |
| 6,496,718 B1 | 12/2002 | Lonky | |
| 6,810,184 B2 | 10/2004 | Skutnik | |
| 6,963,688 B2 | 11/2005 | Nath | |
| 2007/0292098 A1* | 12/2007 | Kokkinos | 385/139 |
| 2008/0045797 A1 | 2/2008 | Yasushi et al. | |

* cited by examiner

*Primary Examiner* — Brian M. Healy
*Assistant Examiner* — Hung Lam
(74) *Attorney, Agent, or Firm* — Pitts, Lake & Bell, P.C.

(57) ABSTRACT

A light-diffusing safety cap for use with a light cable that couples an endoscope to a high intensity light source. The light-diffusing safety cap can be detachably or releasably coupled, in lieu of the endoscope, to the light cable, such that when the high intensity light source emits a high intensity light and the endoscope is not connected to the light cable, the light-diffusing safety cap reduces the intensity of the high intensity light emitted to the environment and provides an indication that the high intensity light source is activated when the endoscope is not connected to the light cable.

6 Claims, 8 Drawing Sheets

LIGHT-DIFFUSING SAFETY CAP

CROSS-REFERENCE TO RELATED APPLICATIONS

This application claims priority from and is a continuation-in-part of U.S. Utility patent application Ser. No. 12/435,479, filed May 5, 2009.

STATEMENT REGARDING FEDERALLY-SPONSORED RESEARCH OR DEVELOPMENT

Not Applicable

BACKGROUND OF THE INVENTION

1. Field of Invention

This invention relates to a safety cap for a light cable connected to a high intensity light source.

2. Description of the Related Art

An endoscope is a medical imaging device that allows a doctor to internally examine a patient. In modern endoscopes, the endoscope is attachable to a high intensity light source via a light guide, or a universal cord, that carries high intensity light produced by the external high intensity light source. These high intensity light sources vary in types and intensity, but generally the high intensity light sources can produce high intensity light having at least 150 watts and may exceed 300 watts. In many commonly used applications, the light guide comprises a fiber optic light cable (hereinafter "light cable"). Such a light cable may be said to have a first end (proximal end), designed to attach to the high intensity light source, and a second end (distal end), designed to attach to the endoscope.

The light cables are disconnectable from the endoscope and external high intensity light source such that each may be cleaned, stored, or transported. For subsequent use of the endoscope, the light cable must be re-connected to the high intensity light source and the endoscope. When a light cable is connected to the high intensity light source but is not yet connected to the endoscope, there exists a danger of starting a fire or causing thermal injury to a person. A standard light cable, when connected to a standard 300 W surgical high intensity light source, can produce temperatures of over 400 degrees Fahrenheit at the distal end of the light cable (i.e. the end not connected to the high intensity light source, or the end that is adapted to be connected to the endoscope). If the distal end of a light cable is left unattended and resting against flammable material, such as surgical drapes, then the light cable in some instances will ignite a fire or burn a patient's skin in a matter of seconds.

A safety problem occurs when one end of the light guide is connected to an activated high intensity light source while the other end is unconnected and emitting high intensity light. This is a significant danger when the high intensity light emitting from the disconnected end of the light guide comes into contact with persons or inflammable materials within the surgery area, e.g. patients and drapes, for a selected period of time. Drapes and gowns, most likely being paper or fabric, are inflammable such that exposure to the high intensity light can ignite the drapes within seconds. Furthermore, a person exposed to the high intensity light in a concentrated area for a selected period can likely suffer thermal injuries. Notably, patients under anesthesia are more likely to receive severe thermal injuries because they cannot move away from the high intensity light before they receive thermal injuries.

BRIEF SUMMARY OF THE INVENTION

When a high intensity light source is activated, the light cable emits high intensity light from the disconnected end in a small concentrated area such that the high intensity light is sufficient for thermal injury to a person and combustion of inflammable materials. Disclosed herein is a safety device that directly diffuses heat of the distal end of an endoscopic light cable. In some embodiments, the safety device comprises a safety cap that acts as a plug for the distal end of an activated light cable (i.e. a light cable in which the proximal end is connected to a high intensity light source and the light source is emitting light). The safety cap is fabricated from an optically translucent material, such as polytetrafluoroethylene or Teflon. The safety cap is attached to the distal end of the light cable during phases of endoscopic procedures when the light cable is left unattached to the endoscope. The safety cap is capable of being attached to and removed from the light cable when necessary. The safety cap does not attach to any surgical instruments that come into direct contact with a patient. The safety cap is autoclavable and is capable of being fully sterilized and included as part of a standard assortment of tools in a surgical tray.

The safety problem occurs when the light guide is not attached to the endoscope wherein the light cable has a disconnected end that is frequently placed beside a patient or object within the surgical area. When the high intensity light source is activated, the light cable emits high intensity light from the disconnected end in a small concentrated area such that the high intensity light is sufficient for thermal injury to a person and combustion of inflammable materials (hereinafter collectively referred to as "thermal harm").

To reduce the likelihood of the light cable causing thermal harm, the light-diffusing safety cap is releasably coupled or detachably installed to the light cable when the endoscope is disconnected. The light-diffusing safety cap is compact and can be attached to the light cable prior to delivery such that the light-diffusing safety cap is coupled to prevent hazards. The light-diffusing safety cap has a diffusing member for receiving the high intensity light from the first end of the light cable and then reducing the intensity thereof. In some embodiments, the diffusing member includes a material to diffuse the high intensity light and emits a reduced intensity light. In some embodiments, the diffusing member includes a material that absorbs high intensity light to reduce the intensity thereof. In some embodiments, the diffusing member has a wall defining a cavity within the diffusing member. The cavity is selectively arranged such that high intensity light is diffused along the cavity.

Reducing the intensity of the high intensity light, whether by diffusing or absorbing, causes a reduced intensity light to be emitted from the light-diffusing safety cap that provides a notification of a potential safety hazard. The reduced intensity light is safe for contact with things or persons within the surgery area, e.g. drapes and patients. The light-diffusing safety cap reduces the likelihood igniting drapes or other inflammable materials and the likelihood of a person suffering burns in the event of inadvertent contact with the high intensity light. Additionally, the diffusing member illuminates for further reducing the likelihood of exposing the unconnected end of the light cable such that high intensity light is emitted causing a safety hazard.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A light-diffusing safety cap for use with a light cable that couples an endoscope to a high intensity light source is disclosed. The light-diffusing safety cap is coupled, in lieu of the endoscope, to the light cable. When activated, the high intensity light source emits a high intensity light that is sufficient to cause thermal harm within a selected time. The light-diffusing safety cap reduces the intensity of the high intensity light to inhibit thermal harm and emits the reduced intensity light to provide an indication that the high intensity light source is activated.

Figure 1:
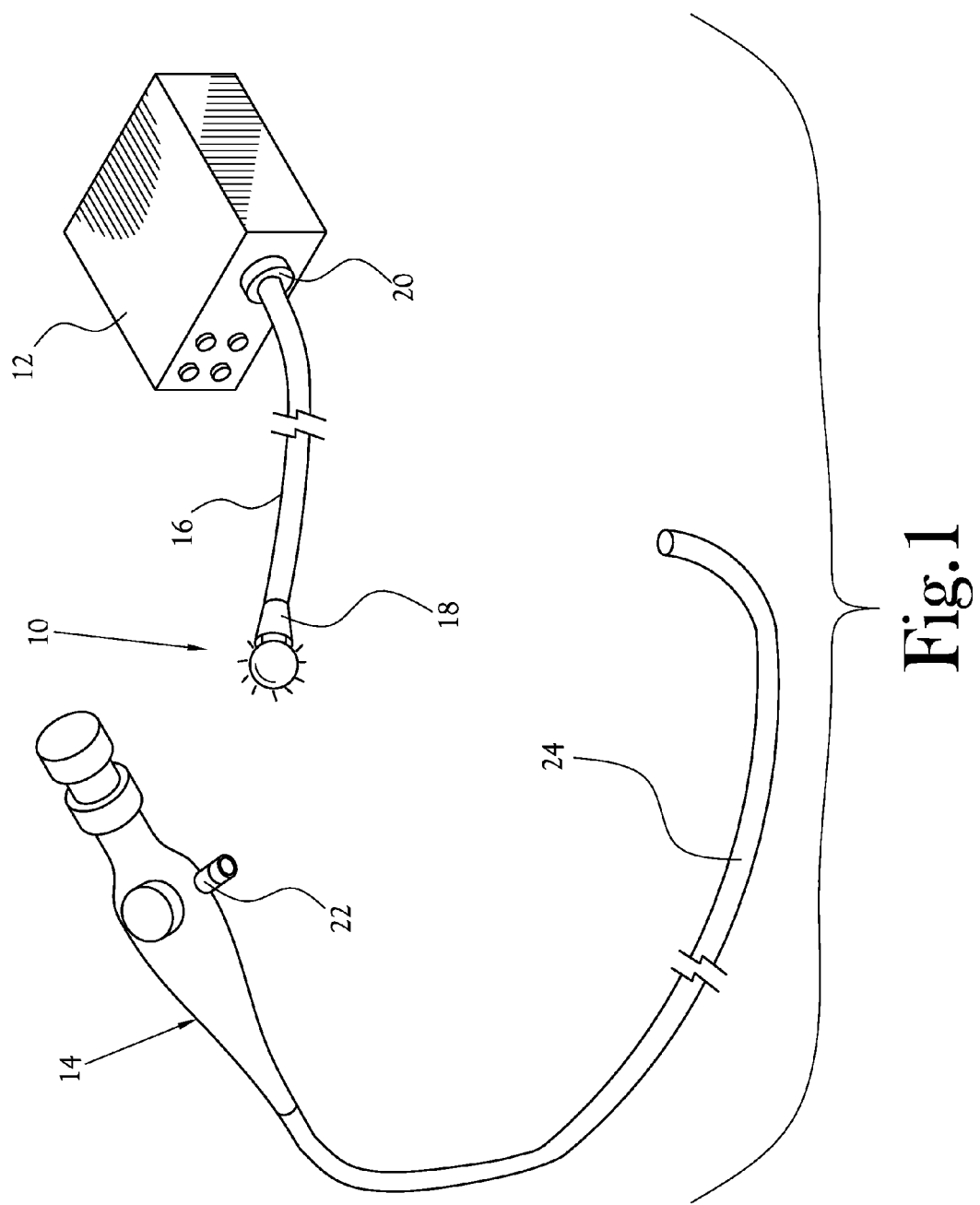
FIG. 1 illustrates an endoscopy system using one embodiment of the light-diffusing safety cap releasably coupled to a light cable.

FIG. 1 illustrates an endoscopy system using one embodiment of the light-diffusing safety cap illustrated generally at 10. The endoscopy system includes a high intensity light source 12, an endoscope 14, and a light cable 16 configured to couple the endoscope 14 to the high intensity light source 12. A first end of the light cable has a first connector 18 configured to connect to an endoscope, and a second end of the light cable has a second connector 20 is configured to connect to a high intensity light source 12. The endoscope 14 having a light-input connector 22 coupleable with the first connector 18 of the light cable 16 and an insertion tube 24 to be inserted within a body to view an illuminated area. The high intensity light source 12 capable of emitting a high intensity light sufficient to cause thermal harm within a selected time. The amount of time that must occur before thermal harm occurs varies with the intensity. At typical operating intensities, the high intensity light is capable of rapidly causing thermal harm. In fact, thermal harm can occur within seconds.

Figure 2:
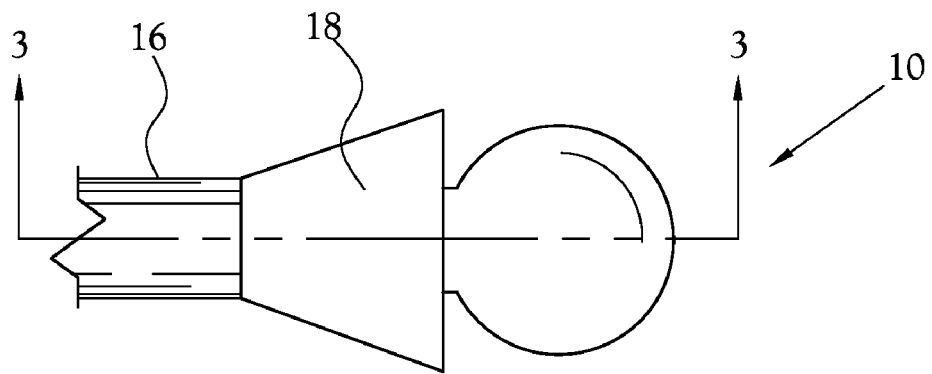
FIG. 2 is a perspective view of one embodiment of the light-diffusing safety cap releasably coupled to a light cable.

FIG. 2 illustrates one embodiment of the diffusing safety cap 10 coupled to the light cable 16. In the illustrated embodiment, a portion of the light-diffusing safety cap 10 is received in the first connector 18 such that the light-diffusing safety cap 10 is coupled within the light cable 16.

Figure 3:
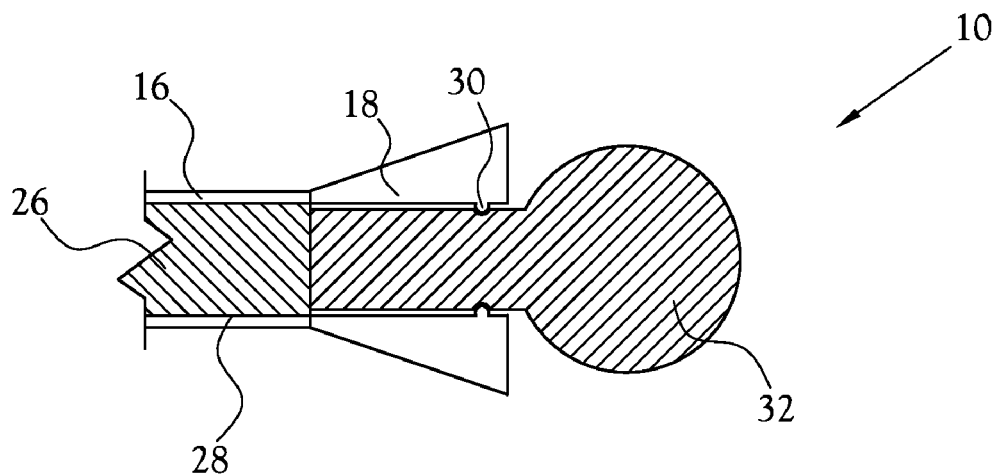
FIG. 3 is a sectional view of one embodiment of the safety cap releasably coupled to a light cable as illustrated in FIG. 2.

FIG. 3 illustrates a sectional view of one embodiment of the safety cap 10 coupled to a light cable 16 for demonstrative purposes. As is apparent from the sectional view, the light cable 16 includes an optical medium 26 through which optical communication occurs. For example, this optical medium 26 can be glass fibers, plastic, or other optical materials. The light cable 16 has a jacket 28 to protect the optical medium 26 from breakage and to aid in reflection such that losses associated with optical communication are reduced. Furthermore, the light cable 16 has a first connector 18 that allows for releasably coupling with the light cable 16. Typically the endoscope is coupled to the light cable 16 wherein the light-input connector 22 is received within the first connector 18 of the light cable 16 such that the circumferential lip 30 engages the groove on the light-input connector 22 and thereby couples the endoscope 14 to the light cable 16.

The light-diffusing safety cap 10 is releasably coupleable to the first connector 18 of the light cable 16 such that light is transmitted there between. In the illustrated embodiment, the safety cap 10 is configured much akin to the light-input connector 22 of the endoscope 14. In the illustrated embodiment, the safety cap 10 is releasably coupleable to the first connector 18 of the light cable 16 such that a portion of the safety cap 10 is disposed proximate to the optical medium 26. This allows for the high intensity light to be transferred from the optical medium 26 into the safety cap 10. In the illustrated light cable 16, the high intensity light travels within the optical medium 26 such that the high intensity light does not travel normal (perpendicular) to the safety cap 10. More specifically, the high intensity light encounters the safety cap 10 at a plurality of angles of incidence such that any space between the optical medium 26 and safety cap 10 can result in reflection of the high intensity light into the optical medium 26. Therefore, as shown in the illustrated embodiment, the safety cap 10 and the optical medium 26 are abutting such that reflection of the high intensity light into the optical medium 26 is reduced.

The light-diffusing safety cap 10 reduces the intensity of the high intensity light such that such thermal harm is inhibited and emits a reduced intensity light that provides an indication that the high intensity light source 12 is active. In some embodiments, the safety cap 10 reduces the intensity of the high intensity light by diffusing the light. The safety cap 10 includes a diffusing member 32 for reducing the intensity of the light. In the illustrated embodiment, the diffusing member 32 is a translucent material that diffuses the high intensity light. In some embodiments, the diffusing member 32 comprises an internal surface to diffuse the received light. In some embodiments, the diffusing member 32 comprises a translucent plastic which diffuses the high intensity light and also absorbs a portion of high intensity light further reducing the intensity thereof. In some embodiments, the diffusing member 32 comprises a transparent material, such as Pyrex glass, that is frosted to diffuse the high intensity light such that a selected amount of high intensity light passes through the diffusing member 32. The reduced intensity light is thereafter emitted from the safety cap 10. Additionally, in some embodiments of the safety cap 10, emissions of reduced intensity light provide an indication that the high intensity light source 12 is active. In some embodiments, the safety cap 10 provides an indication by the diffusing member 32 absorbing a portion of the light such that the diffusing member 32 "glows" from the absorbed light.

Figure 4:
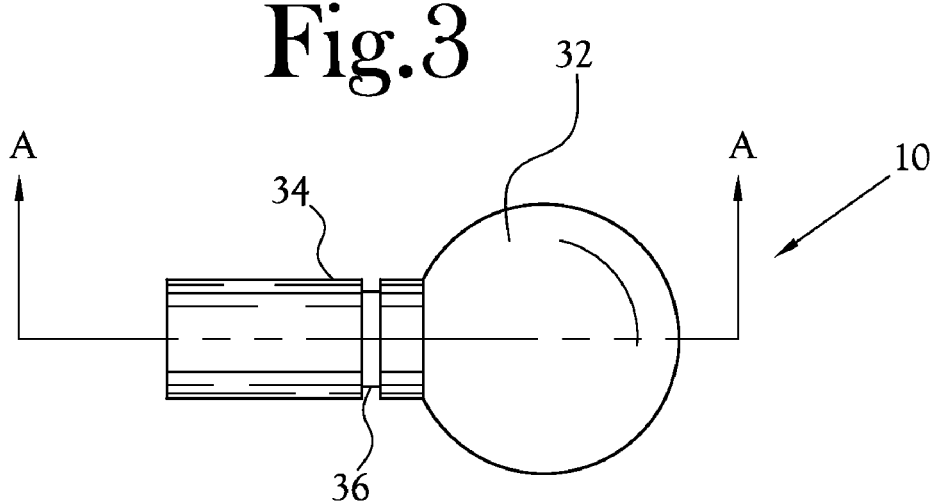
FIG. 4 is a perspective view of one embodiment of the safety cap.

FIG. 4 illustrates one embodiment of the light-diffusing safety cap 10 having a diffusing member 32 and member 34 for coupling, mounting or attaching the safety cap 10 to the light cable 16 (hereinafter this member 34 is referred to as a "coupling member"). The coupling member 34 is configured such that the coupling member 34 is releasably coupleable to the first connector 18 of the light cable 16. More specifically, the coupling member 34 has a groove 36 about the coupling member 34 that is engaged by the circumferential lip 30 when the coupling member 34 is received by the first connecter 18 of the light cable 16. The diffusing member 32 is configured such that when coupled to the light cable 16 the diffusing member 32 is in optical communication with the high intensity light source 12. It should be noted, that the diffusing member 32 can be any shape, although shown as spherical in the illustrated Figures, including, but not limited to, conical, square, partially spherical, or other orientation such that the diffusing member 32 can reduce the intensity of the high intensity light. In some embodiments, the diffusing member 32 and coupling member 34 can be one piece, respective pieces, or otherwise be arranged for reducing the intensity of the high intensity light when releasably coupling to a light cable 16.

In some embodiments of the present invention, various devices are used to attach the safety cap to the distal end of the light cable. In some embodiments, the coupling member comprises a threaded male component that mates with a threaded female component affixed to the distal end of a light cable. Persons of skill in the art will recognize that additional coupling mechanisms are compatible with the present invention and are contemplated by this application.

Figure 5:
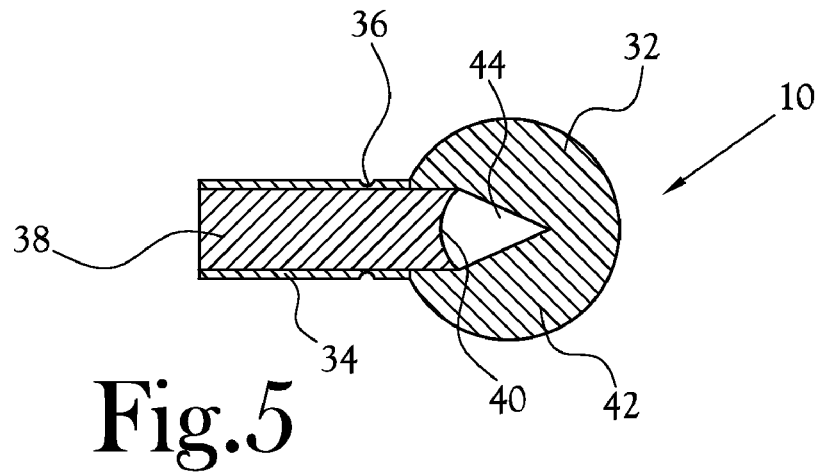
FIG. 5 is a sectional view of one embodiment of the safety cap releasably coupled to a light cable as illustrated in FIG. 4.
Figure 6:
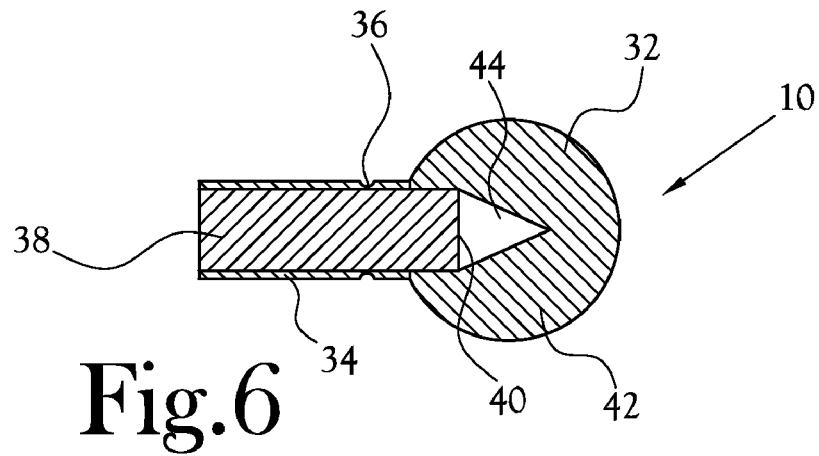
FIG. 6 is a sectional view of one embodiment of the safety cap releasably coupled to a light cable as illustrated in FIG. 4.
Figure 7:
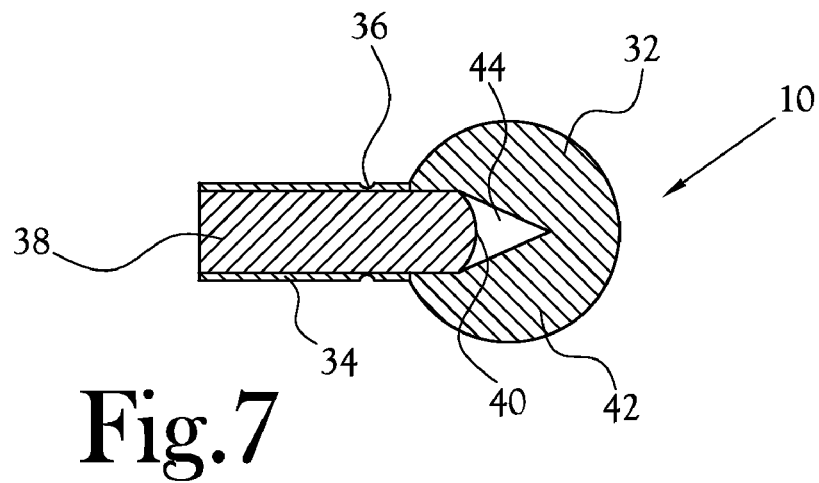
FIG. 7 is a sectional view of one embodiment of the safety cap releasably coupled to a light cable as illustrated in FIG. 4.

FIGS. 5-7 illustrate embodiments of a sectional view at A in one embodiment of the safety cap 10. The safety cap 10 is releasably coupleable with a light cable 16 to reduce the intensity of the high intensity light such that such thermal harm is inhibited and said safety cap 10 provides an indication that high intensity light is being received by the safety cap 10. In the illustrated embodiments, the safety cap 10 includes a coupling member 34, a cylindrical member 38, and a diffusing member 32.

The coupling member 34 releasably couples the light-diffusing safety cap 10 with the light cable 16. In the illustrated embodiments, the coupling member 34 being a cylindrically hollow member receivable within the first connector 18 of the light cable 16. The coupling member 34 being receivable within the first connector 18 of the light cable 16 such that circumferential lip 30 engages the groove 36 of the coupling member 34 and thereby releasably coupling the light-diffusing safety cap 10 to the light cable 16. In alternate embodiments, the light-diffusing safety cap 10 is otherwise disposed proximate to the end of the light cable 16 without departing from the spirit and scope of the present invention.

The cylindrical member 38 is securable within the coupling member 34 such that light emitted by the light cable 16 is received by the cylindrical member 38 which transfers the light to the diffusing member 32. In the illustrated embodiments, the cylindrical member 38 is a transparent material such that light passes, relatively unaffected, into the diffusing member 32. Furthermore, the cylindrical member 38 defines a lens 40 for defining how the high intensity light passes into the diffusing member 32. In the illustrated embodiment, the lens 40 is selected from concave (FIG. 5), flat (FIG. 6), or convex (FIG. 7) such that light is focused or spread upon entering the diffusing member 32. In alternative embodiments, the lens 40 can be frosted such that the intensity of high intensity light is further reduced upon entering the diffusing member 32.

The diffusing member 32 reduces the high intensity light such that reduced intensity light is emitted from the diffusing member 32. The diffusing member 32 is releasably coupled with the cylindrical member 38 such that high intensity light from the light cable 16 is transferred through the cylindrical member into the cavity of the diffusing member 32. In the illustrated embodiment, the diffusing member 32 is generally translucent and has a wall 42 defining a cavity 44 within the diffusing member 32. The cavity 44 is selectively arranged such that high intensity light is diffused along the cavity 44. In the illustrated embodiment, the cavity 44 is conically shaped such that high intensity light from the cylindrical member 38 enters the cavity 44 through the cone's base and travels outward. As the high intensity light progresses through the cavity 44 the high intensity light impacts the wall 42, of the diffusing member 32, along the locus of the cavity 44 such that rays of light are scattered outward through the wall 42 in multiple directions and thereby emitting reduced intensity light. In alternate embodiments, the diffusing member 32 can reduce the intensity of the high intensity light in ways other than those described above without departing from the spirit and scope of the present invention.

Figure 8:
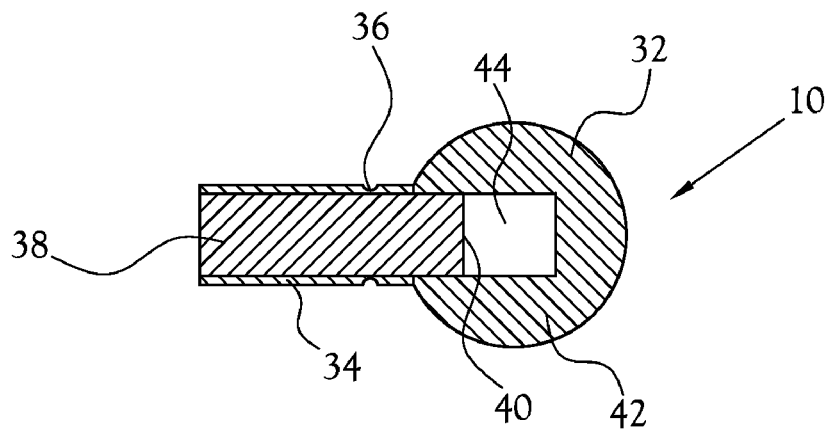
FIG. 8 is a sectional view of an alternate embodiment of the safety cap releasably coupled to a light cable as illustrated in FIG. 4.

FIG. 8 illustrates an alternate embodiment of a sectional view at A in one embodiment of the light-diffusing safety cap 10. The cylindrical member 16 has a flat lens 40 being frosted such that reduced intensity light passes into the diffusing member 32. The diffusing member 32 being translucent and absorbing and having a wall 32 that defines a cubic cavity 44 within the diffusing member 32. The cavity 44 and wall 42 contribute to reduction of the light intensity. In an alternate embodiment, the cylindrical member 38 is receivable within the diffusing member 32 such that the cylindrical member 38 occupies the shown cavity 44. More specifically, the cylindrical member 38 is inserted into the diffusing member 32 and bonded by thermally annealing the cylindrical member 38 to the diffusing member 32.

Figure 9:
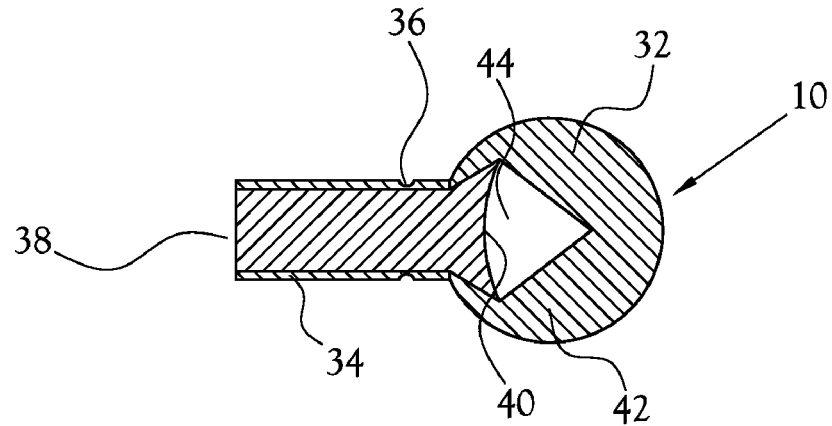
FIG. 9 is a sectional view of an alternate embodiment of the safety cap releasably coupled to a light cable as illustrated in FIG. 4.

FIG. 9 illustrates an alternate embodiment of a sectional view at A in one embodiment of the light-diffusing safety cap 10. The cylindrical member 38 has a concave lens 40 through which light passes into a conical cavity 44 within the diffusing member 32. The lens 40 of the cylindrical member 38 is flared outward to capture additional high intensity light for focusing into the cavity 44.

Figure 10:
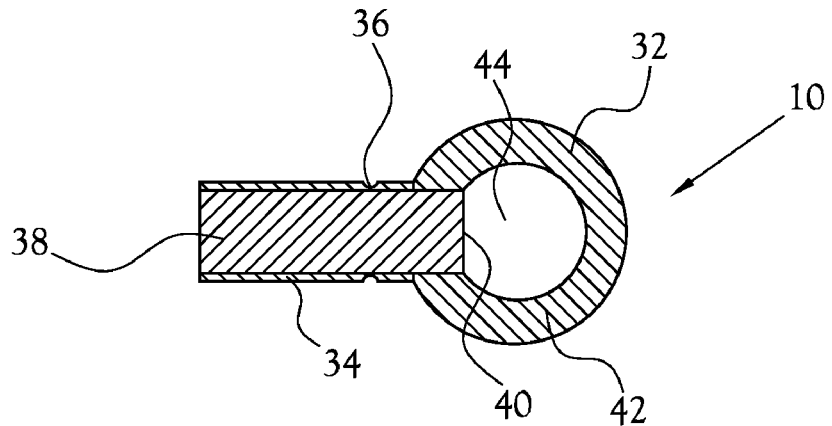
FIG. 10 is a sectional view of an alternate embodiment of the safety cap releasably coupled to a light cable as illustrated in FIG. 4.

FIG. 10 illustrates an alternate embodiment of a sectional view at A in one embodiment of the light-diffusing safety cap 10. The cylindrical member 38 has a flat lens 40 through which high intensity light rays pass into a spherical cavity 44 within the diffusing member 32. As the high intensity light progresses through the cavity 44 rays of high intensity light impact the wall 42, of the diffusing member 32, along the curvature of the cavity 44 such that the rays of high intensity light are scattered outward through the wall 42 of the diffusing member 32 in multiple directions and thereby emitting reduced intensity light.

Figure 11:
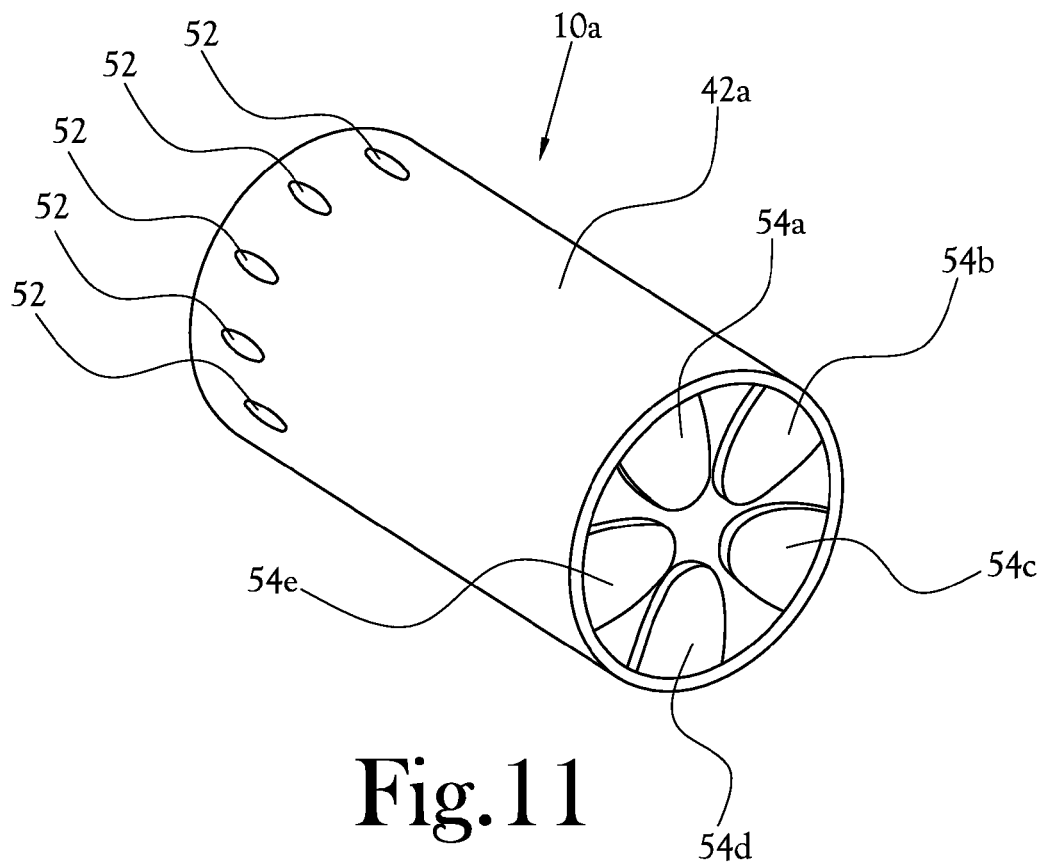
FIG. 11 is a perspective view of one embodiment of a the present invention.
Figure 12:
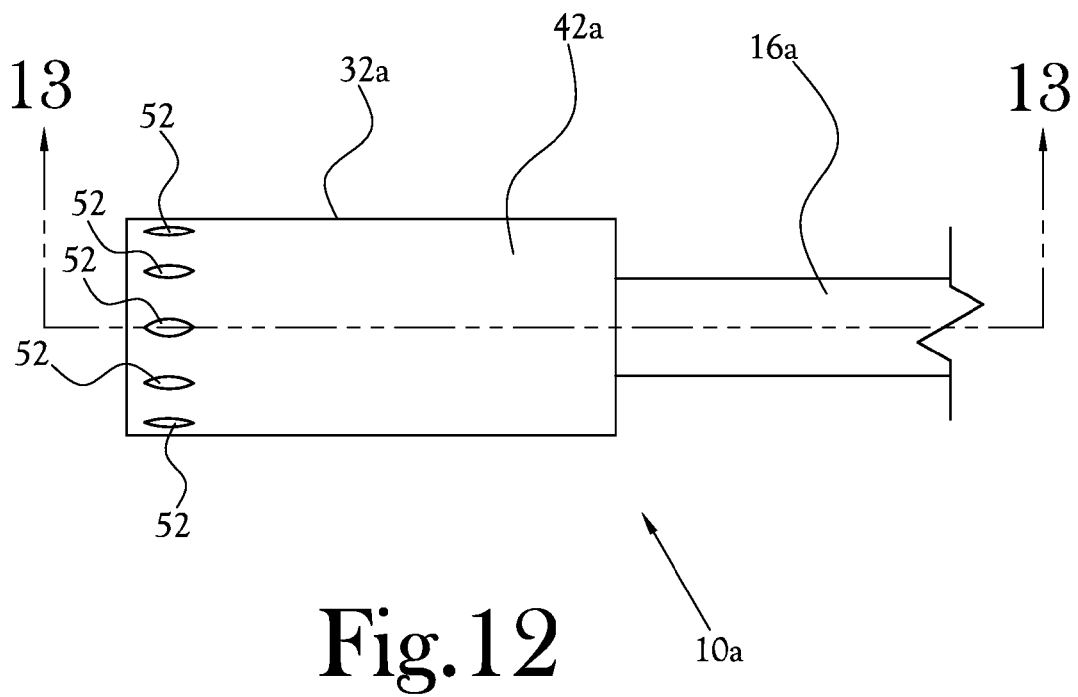
FIG. 12 is a side view of the embodiment illustrated in FIG. 11.
Figure 13:
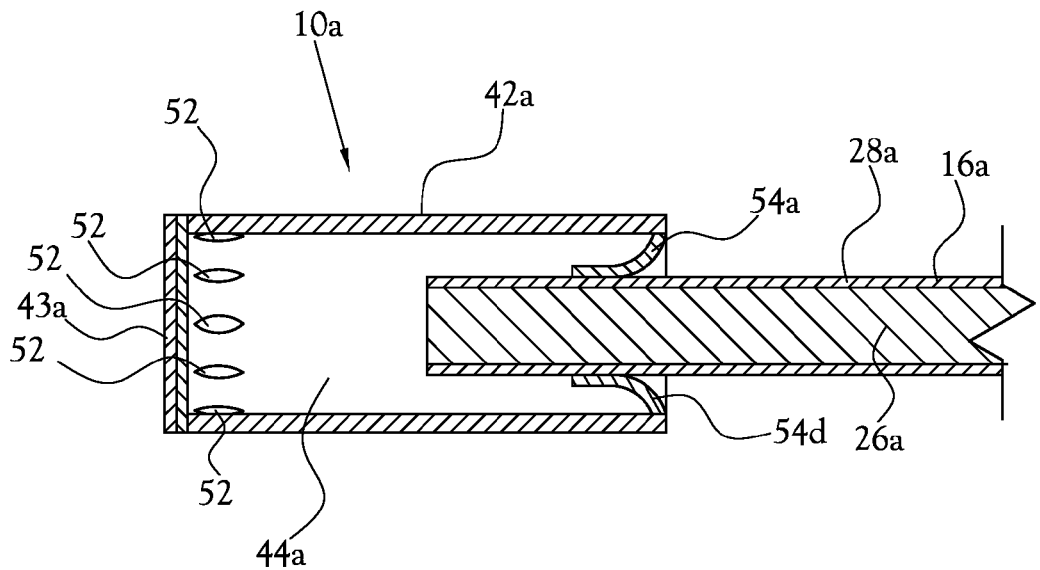
FIG. 13 is a sectional view of the embodiment illustrated in FIGS. 11 and 12.

FIG. 11 illustrates one embodiment of the present invention. FIG. 12 shows a side view of the same embodiment, and FIG. 13 provides a sectional view of the embodiment. In this embodiment, a safety cap 10a is adapted to fit with a light cable 16a that does not include the first connector 18 shown in FIGS. 1-3. The light cable 16a does include an optical medium 26a and a jacket 28a. As seen most clearly in FIG. 13, the safety cap 10a includes a diffusing member 32a that comprises a cylindrical wall 42a and an end member 43a; the surrounding wall 42a defines a cavity 44a that receives the distal end of the light cable 16a. As shown in FIG. 11, the safety cap 10a includes a number of pressure flaps 54a-e. FIG. 13 shows how, when the light cable 16a is inserted into the cavity 44a, the pressure flaps 54a-e bend to receive the light cable 16a in a pressurized fit. In some embodiments, the diffusing member 32a is fabricated from Teflon or from a translucent material. In some embodiments, the end member 43a of the safety cap 10a is thicker than the wall 42a, since at most times a substantial majority of the light and heat emanating from the light cable 16a is directed at the end member 43a. In some embodiments, the diffusing member 32a includes ventilation holes 52 cut into wall 42a; the ventilation holes 52 help to prevent the safety cap 10a from becoming overheated when the light cable 16a is activated. The safety cap 10a illustrated at FIGS. 11-13 has the advantage of being adaptable to light cables with a variety of cable diameters. In some embodiments, the safety cap 10a is disposable.

Figure 14:
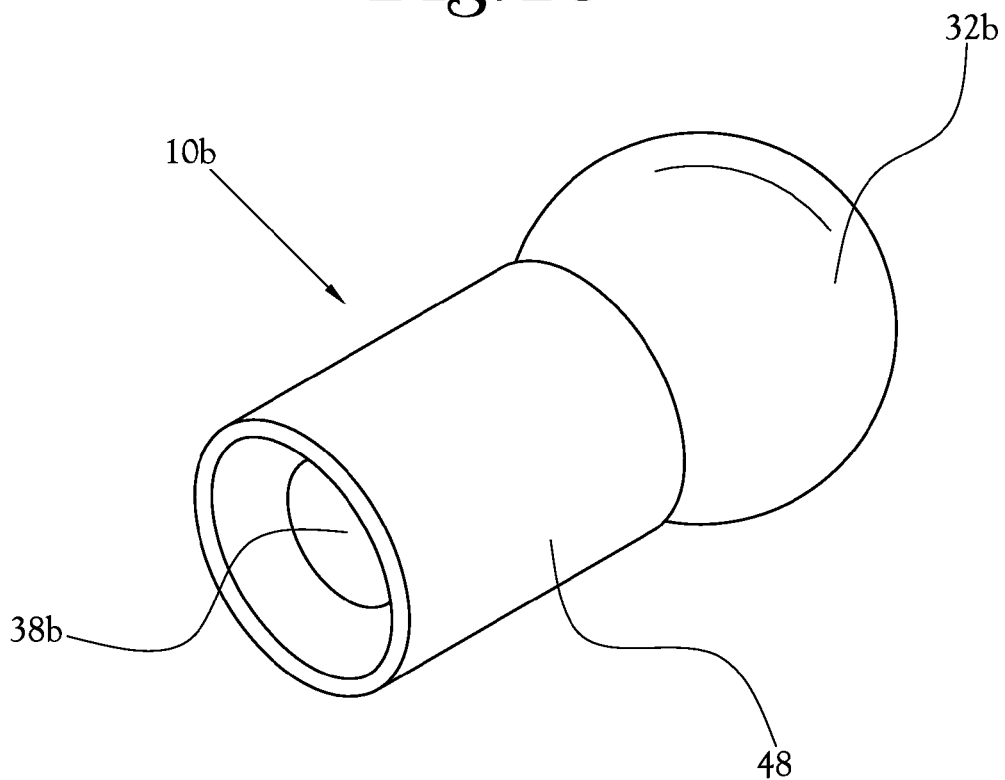
FIG. 14 is a perspective view of one embodiment of the present invention.
Figure 15:
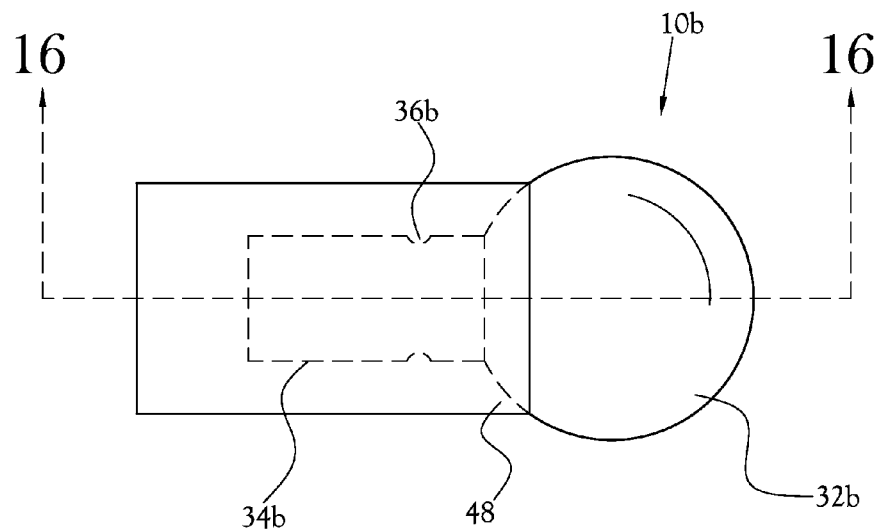
FIG. 15 is a side view of the embodiment illustrated in FIG. 14.
Figure 16:
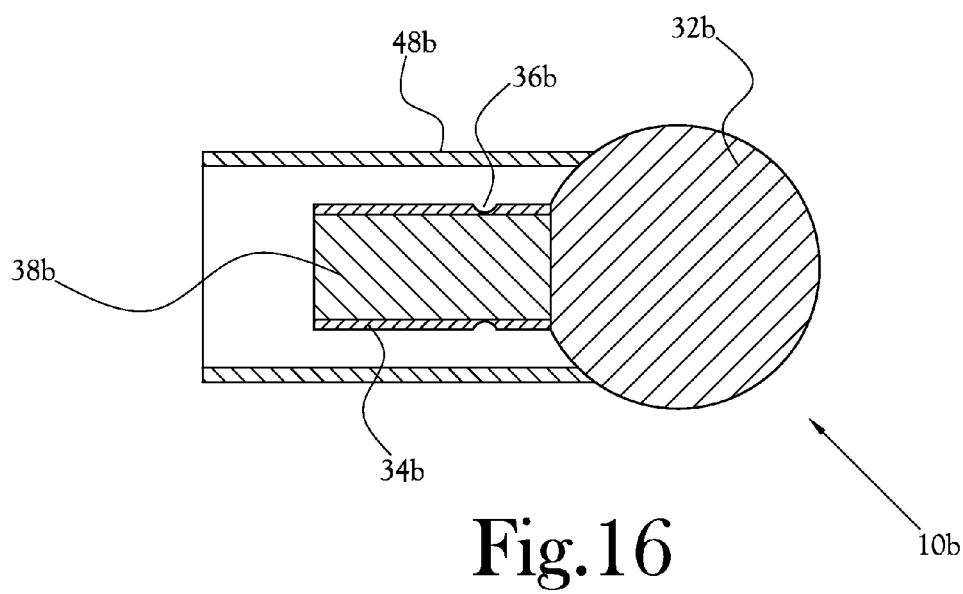
FIG. 16 is a sectional view of the embodiment illustrated in FIGS. 14 and 15.

FIGS. 14-16 illustrate one embodiment of the present invention. As with the embodiments shown in FIGS. 2-4, a safety cap 10b includes a diffusing member 32b and coupling member 34b, with the coupling member 34b configured such that the coupling member 34b is releasably coupleable to a connector of a light cable. As seen in the section view in FIG. 16, the coupling member 34b includes a cylindrical member 38b and a groove 36b about the coupling member 34b that is engaged by a circumferential lip of the connector of the light cable when the coupling member 34b is received by the connecter of the light cable. In this embodiment, the safety cap 10b further features a jacket 48, in many cases fabricated from a flexible thermal insulator; the jacket 48 surrounds the connector and distal end of the light cable when the safety cap 10b is attached to the light cable.

Figure 17:
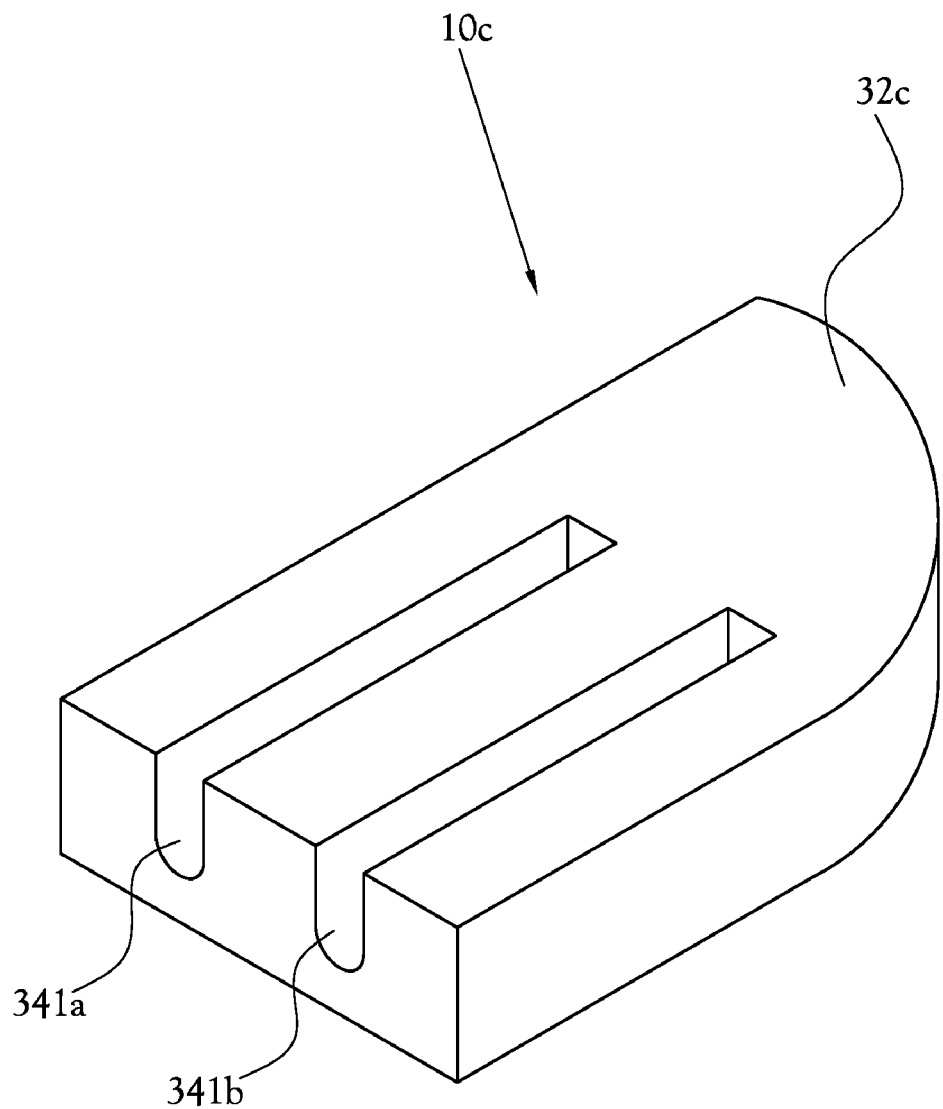
FIG. 17 is a perspective view of one embodiment of the present invention.

FIG. 17 illustrates one embodiment of the present invention. In the illustrated embodiment, the device 10c comprises a single member 32c with a flat resting surface. On a surface opposite the resting surface, two receptacles 341a and 341b are defined by grooves in the material of the device 10c. The member 32c is fabricated from Teflon or from a translucent material that will diffuse light from the distal end of a light cable placed into one of the receptacles 341a and 341b. In some embodiments, the receptacles 341a and 341b have different widths so as to receive light cables of differing diameters.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A light-diffusing safety cap for use with a light cable having a first end and a second end, the first end configured to connect to a high intensity light source, the second end configured to connect to a endoscope, said safety cap comprising:
   a coupling member to releasably attach said safety cap to the second end of the light cable when the endoscope is not connected to the light cable, and
   a diffusing member to receive light from the high intensity light source via the light cable when the endoscope is not connected to the light cable, said diffusing member having an internal surface to diffuse the received light to reduce the intensity of the received light, and to emit the diffused light to an outside of the diffusing member when the endoscope is not connected to the light cable to provide an indication that the high intensity light source is activated, said diffusing member including a wall to define said internal surface such that when the high intensity light is received into said internal surface, said wall scatters rays of light outward through said wall to emit a lower-intensity light to the outside of the diffusing member.

2. The light-diffusing safety cap of claim 1 wherein said internal surface comprises a conical shape tapered away from the first end of the light cable.

3. A light-diffusing safety cap for use with a light cable having a first and a second end, the first end configured to connect to a endoscope, the second end configured to connect to a high-intensity light source, said light-diffusing safety cap comprising:
   a mounting member to releasably couple the safety cap to the first end of the light cable when the endoscope is not connected to the light cable; and
   a diffusing member carried by said mounting member to receive a first intensity light from the light source via said light cable when said endoscope is not connected to said light cable, to reduce the first intensity light to a second intensity light for a selected period of time, and to emit said second intensity light to an outside of the diffusing member to provide an indication that the high intensity light source is active, said diffusing member including a wall that defines an internal cavity, such that when the first intensity light is received into said internal cavity, said wall scatters rays of the first intensity light outward through said wall to emit the second intensity light to the outside of the diffusing member.

4. In an endoscopic system including a high intensity light source, an endoscope, and a light cable adapted to transmit light from the high intensity light source to the endoscope, the light cable having a first end adapted to connect with the high intensity light source and a second end adapted to connect with the endoscope, a method of reducing the intensity of light emitted from the light source via the light cable when the endoscope is not connected to the light cable, said method comprising:
   connecting the first end of the light cable to the high intensity light source;
   connecting the second end of the light cable to a light-diffusing safety cap when the endoscope is not connected to the light cable, said light-diffusing safety cap including an internal surface to diffuse the received light;
   activating the high intensity light source; and
   emitting the diffused light from the light-diffusing safety cap via the internal surface to an outside of the light-diffusing safety cap to provide an indication that the high intensity light source is activated.

5. The method of claim 4 wherein the method further comprises disconnecting the second end of the light cable from said light-diffusing safety cap and immediately thereafter connecting the second end of the light cable to the endoscope.

6. The method of claim 5 wherein the method further comprises disconnecting the second end of the light cable from the endoscope and immediately thereafter connecting the second end of the light cable to said light-diffusing safety cap and deactivating the high intensity light source.

* * * * *